United States Patent [19]

Griffiths et al.

[11] Patent Number: 4,937,199
[45] Date of Patent: Jun. 26, 1990

[54] DETECTION OF VIRUSES AND ANTIBODIES

[75] Inventors: Paul D. Griffiths; Jane E. Grundy; Jane A. McKeating, all of London, England

[73] Assignee: The Royal Free Hospital School of Medicine, London, England

[21] Appl. No.: 939,044

[22] PCT Filed: Mar. 17, 1986

[86] PCT No.: PCT GB86/00155

§ 371 Date: Jan. 14, 1987

§ 102(e) Date: Jan. 14, 1987

[87] PCT Pub. No.: WO86/05593

PCT Pub. Date: Sep. 25, 1986

[30] Foreign Application Priority Data

Mar. 18, 1985 [GB] United Kingdom .............. 8506942
May 24, 1985 [GB] United Kingdom .............. 8513211

[51] Int. Cl.$^5$ .............. G01N 33/571; G01N 33/543; G01N 33/53; C12Q 1/70
[52] U.S. Cl. ............................ 436/511; 436/518; 436/547; 436/548; 436/825; 435/5; 435/6; 435/7
[58] Field of Search ............... 436/511, 518, 529, 548, 436/825; 435/5

[56] References Cited

U.S. PATENT DOCUMENTS

| | | | |
|---|---|---|---|
| 3,839,153 | 10/1974 | Schuurs et al. | 436/518 |
| 4,185,084 | 1/1980 | Mochida et al. | 436/518 |
| 4,341,754 | 7/1982 | Kaplan et al. | 424/1 |
| 4,358,535 | 11/1982 | Falkow et al. | 435/5 |
| 4,455,381 | 6/1984 | Magnusson et al. | 436/518 |
| 4,617,264 | 10/1986 | Whiteley et al. | 436/511 |
| 4,675,286 | 6/1987 | Calenoff | 436/518 |

FOREIGN PATENT DOCUMENTS

| | | |
|---|---|---|
| 0097633 | 6/1983 | European Pat. Off. . |
| 0139416 | 8/1984 | European Pat. Off. . |
| 0180288 | 5/1985 | European Pat. Off. . |

OTHER PUBLICATIONS

Davey et al., "B2-Microglobulin Instability in Pathological Urine", Clin. Chem., 28(6), 1330–1333, 1982.
J. Gen. Virol., 68, 793–803, (1987), p. 793 only.
Journal of Medical Virology, 16: 367–373, (1985).
Journal of Medical Virology, 18:341–348, (1986), p. 341 only.
Chemical Abstracts, vol. 94, p. 471, (1981).
J. Gen. Virol., 68, 777–784, (1987), p. 777 only.
J. Gen. Virol., 68, 785–792, (1987), p. 785 only.
Biochem. J., 241, 313–324, (1987).
Chemical Abstracts, vol. 98, p. 494, (1983).
Chemical Abstracts, vol. 101, p. 604, (1984).

Primary Examiner—Robert J. Warden
Assistant Examiner—Ganell Graeter
Attorney, Agent, or Firm—Irell & Manella

[57] ABSTRACT

An improved method of detecting, in a beta$_2$m containing clinical sample, a virus of the herpes group or an antibody to that virus, by assaying the sample with a reagent that will reveal the presence of the virus or antibody comprising, utilizing or removing the beta$_2$m prior to the assay by (1) removing beta$_2$m from at least the sample and reagent, or
(2) contacting a sample that is to be assayed for virus with a reagent that reacts with beta$_2$m and which will form an anti-beta$_2$m/beta$_2$m/virus conjugate.

21 Claims, 10 Drawing Sheets

DETECTION OF VIRUSES AND ANTIBODIES

This invention relates to a method for the detection of viruses or virus antibodies and is particularly concerned with the detection of viruses of the Herpes group and their antibodies.

The Herpes group of viruses are a group of considerable clinical significance, the most important members of the group being Herpes Simplex (HSV), Cytomegalovirus (CMV), Epstein Barr virus (EBV) and Varicella-zoster virus (VZV). Infections with CMV occur frequently in the United Kingdom so that 60% of adults have evidence of past infection. Occasionally, the virus produces cases of Paul Bunnell negative glandular fever but the vast majority of infected people remain entirely asymptomatic. This virus infection is therefore primarily of medical importance in specific groups of patients which are neonates with congenital infection, and immunocompromised individuals, such as recipients of renal or bone marrow allografts or patients with the acquired immunodeficiency syndrome (AIDS). In each of these groups of patients, CMV is an important pathogen and it would be very desirable, from the clinical point of view, to have available an assay method that can reliably identify the presence of CMV and the amount of CMV present in clinical samples.

Various methods have been proposed in the past for assaying CMV in samples of blood, urine or saliva taken from patients suspected of having CMV infection. Several methods have been proposed previously for the identification of CMV involving indirect assay by cultivating the virus in tissue culture and by methods involving the use of polyclonal antibodies and monoclonal antibodies that recognise the virus. The major difficulty, at the practical level, has been that while the various assay methods have been found to work and to provide reproducible and reliable data when carried out on model experimental systems which are artificially infected with CMV, the same methods do not provide equally reliable and reproducible results when carried out on clinical samples suspected to contain or known to contain CMV.

We have investigated the possible reasons for this disparity of performance of assay methods between experimental model systems and clinical samples and we have identified what we believe to be the presence of an inhibitory material associated with CMV in the clinical environment which prevents reliable and reproducible results being obtained by the various assay systems that have been developed.

We have discovered that in the clinical environment, molecules of beta$_2$microglobulin become associated with the outer envelope of CMV and mask the antigenic determinants that are present on the surface of CMV so making unreliable the identification of CMV by the use of antibodies that normally recognise CMV. Beta$_2$microglobulin is a protein that exists in urine and other body fluids that are normally assayed for CMV and we believe that this masking effect, rendering the antigenic determinants on the outer envelope unavailable for recognition by antibodies that normally recognise such determinants, will occur with the other Herpes group viruses, HSV, EBV and VZV which all contain outer envelopes of the type possessed by CMV.

As an alternative to the direct detection of the Herpes group virus, diagnostic methods are available which involve the detection of antibody to the herpes virus. Such antibody detection methods normally involve the use of known quantities of viral antigen, often in insolubilised form, but such antibody detection assays will not necessarily be reliable since any beta$_2$microglobulin (hereinafter called beta$_2$m) associated with the clinical sample will compete with antibody for binding to the viral antigen and can become bound to any insolubilised antigen, so reducing to an unknown extent, the amount of free insolubilised antigen available for binding with the unknown antibody.

Having identified the role played by beta$_2$m in interactions between antibodies and antigens of viruses of the Herpes group, we have recognised that, by taking appropriate precautions, diagnostic methods based upon the detection of surface antigens of a virus of the Herpes group or detection of antibodies to viruses of the Herpes group can be rendered reliable.

Accordingly the present invention provides a method of detection in a beta$_2$m containing clinical sample of a binding partner for which there is a complementary binding partner wherein the complementary binding partners are a virus of the Herpes group and the corresponding antibodies against the virus, which method comprises (1) bringing the sample into contact with a reagent which will reveal the presence of the binding partner to be detected, the sample being freed from beta$_2$m and/or the reagent being free from beta$_2$m; or (2) contacting a sample to be assayed for virus with a reagent that reacts with beta$_2$m and which will form an anti-beta$_2$m /beta$_2$m/virus conjugate and subsequently assaying for virus.

"Free" and "freed" from beta$_2$microglobulin, in relation to the clinical sample and the reagent means that the beta$_2$-microglobulin concentration is sufficiently low to avoid significant interference in the assay. Preferably both the sample is freed from beta$_2$m and the reagent is free from beta$_2$m. Methods of preventing the beta$_2$m from interfering with the binding of the virus and antibody encompasses methods such as physically filtering out the beta$_2$m, using a reagent such as a beta$_2$m-recognising monoclonal or polyclonal antibody on a solid support to "capture" the beta$_2$m, or destroying the beta$_2$m e.g. by degrading it enzymatically.

This invention makes it possible to detect virus antigen or antibody by any of the conventional assay methods used for the qualitative or quantitative assay of unknown antibody using known antigen or assay of unknown antigen using known antibody whilst avoiding the errors introduced in prior art methods by the inhibitory action of the beta$_2$microglobulin. The preferred binding partners used in the method are cytomegalovirus (CMV) and corresponding antibody.

When using the method to detect the presence of the virus we have developed two distinct approaches to solving the problem of the inhibitory substance. The first approach is based on the removal of the inhibitory substance prior to detection of the virus while the second involves capturing the inhibited virus via its inhibiting agent followed by the identification of the virus.

Our first approach, involves degrading the beta$_2$m enzymatically. This approach is particularly well suited to urine samples which we have found contain an enzyme which, at neutral pH, does not influence the beta$_2$m which remains firmly bound to the outer viral envelope but which is activated at acidic pH at 35° to 40° C. and will, under those conditions, bring about degradation of beta$_2$m thus effectively revealing the antigenic determinants on the outer viral envelope for recognition in a subsequent step by an appropriate antibody. When operating in accordance with this approach, it is necessary to add an appropriate pH adjusting agent to the urine sample, for example 1M NaOH or 1M HCl, so that the pH can be adjusted to within the range 5.0 to 7.0, preferably 5.5, and the sample is maintained at elevated temperature, preferably body heat, i.e. 37° C. for at least 1 hour, at which period of time the enzymatic action is sufficiently complete to allow a consistent assay to be carried out on the virus.

Once the beta$_2$m has been removed, we have found that the antigenic determinants on the outer viral coat are available for detection in the same way that they can be detected in the experimental model systems and that consistent results can be obtained by any of the existing detection methods. One preferred method involves an enzyme-linked immunosorbent assay (ELISA) which permits an immunochemical identification. In this assay, a double antibody sandwich is used with either a polyclonal antibody or a monoclonal antibody as the capture antibody, which is bound to a solid support, either microtitre plates or beads. This is then incubated with the specimen and any viral antigens present in the specimen will bind to the capture antibody. The unbound material is washed away and the bound material detected by a suitable antibody (either monoclonal or polyclonal) directed against the viral antigens. The binding of this antibody can then be detected in one of two ways; (1) if this antibody has been directly conjugated to an enzyme, by the addition of a suitable substrate and measurement of optical density change or (2) by the further addition of an enzyme conjugated antibody directed against the species in which the former antibody had been raised. Further details of such an ELISA system are given in the Examples below.

This ELISA technique is capable of detecting tissue culture grown CMV at concentration as low as $10^{2.3}$ $TCID_{50}$/ml which means that this technique when applied in association with our invention, has adequate sensitivity for the detection of CMV in urine samples where it is normally present at a concentration of $10^3$ to $10^6$ $TCID_{50}$/ml.

Other methods of detecting the presence of the virus in clinical samples, once the interfering beta$_2$m has been removed, can also be used, for example radioimmunoassay techniques or immunofluorescent techniques. In principle these techniques are identical to that of the ELISA mentioned above, but utilise either antibodies labelled with $^{125}I$ or fluorescent conjugates, instead of the enzyme conjugated antibodies used in the ELISA. Thus the final detection is by $\gamma$counting or by the observation of fluorescent foci under the UV microscope.

The other approach to overcoming the problem of the antigenic sites on the viral envelope being masked by the beta$_2$m involves the use of a reagent to bind the beta$_2$m. Once the virus/beta$_2$m complex has been bound to the reagent that recognizes beta$_2$m, it is possible to disrupt the virus particle and to make a positive and, if desired, quantitative determination of virus by identification of viral DNA or viral proteins contained within the virus particle.

One practical embodiment of this approach is to utilise a monoclonal antibody that recognizes beta$_2$m as a beta$_2$m capturing agent, where the monoclonal antibody is bound to a solid support. Such monoclonal antibodies include No. HLA. ABCM2 from Serotec Ltd., Oxon, UK or BBM.1 (produced by the hybridoma ATCC Hybridoma No. HB 28). Two strategies can be used to detect the presence of the virus after capture, these being the detection of specific viral proteins by immunoblotting, or the detection of viral DNA by labelled cloned specific CMV DNA probes. Using the latter approach we have found that it is particularly convenient to capture the virus by utilizing a monoclonal antibody which is bound to a solid support such as nitrocellulose paper. Any virus contained in the clinical sample will be "captured" by the monoclonal antibody via the beta$_2$m attached to the viral envelope and the solid-monoclonal antibody viral conjugate may be separated from the sample. Once the virus has been "captured" in this way, the virus particle may be disrupted by treatment with a surface-active agent of the type known to be capable of disrupting virus particles. Such surface-active agents can be cationic detergents such as an alkali metal salt of an alkyl benzene sulphonate. In such cationic detergents, the alkyl group will normally be a higher alkyl group containing 8 to 18 carbon atoms and will normally be a straight alkyl chain and reference may be made to detergents such as sodium dodecyl sulphonate, sodium octyl sulphonate and ammonium hexadecyl sulphonate, ammonium being regarded as an alkali metal for the purposes of viral envelope disruption. Alternatively, use may be made of one of the non-ionic detergents such as one of the Tritons which are polyethoxylated phenols. Once the virus particle has been disrupted in this way, the viral DNA is released onto the surface of the insolubilising material, for example the nitrocellulose paper. At this stage, it is possible to make a positive identification of the viral DNA associated with CMV or other Herpes group virus under investigation by the use of DNA probes. DNA probes which are complementary to the viral genome are available (Oram et al). The DNA probes may be radio-labelled with $^{32}P$ or labelled with biotin. Clinical samples which are positive with respect to the Herpes group virus under investigation will be revealed by the presence of the labelled DNA probe which will become bound to the viral DNA on the paper while samples of the labelled probe which are not complementary to viral DNA present on the probe can be washed away. It is then a simple matter to detect the presence of the bound DNA probe via its revealing label which becomes a positive indication of the presence of virus.

The second strategy of detecting the presence of virus after capture from clinical specimens by antibodies to beta$_2$m involves the detection of viral proteins. One preferred method is to immuno-precipitate the virus/anti beta$_2$m complex using staphylococcal Protein A bound to sepharose or, if biotinylated antibodies are used, streptavidin bound to agarose may be used. These immuno-precipitates can then either be directly spotted onto nitrocellulose filters or the proteins separated by polyacrylamide gel electrophoresis and then transferred onto nitrocellulose paper (a technique referred to as western blotting). These proteins are then detected by antibodies to CMV, either directly labelled (with enzyme or radioactive isotope), or if unlabelled, then a second, labelled, antibody directed against the immunoglobulin of the species in which the former antibody was raised is added. The protein spots or bands are then visualized by autoradiography if a radiolabel such as $^{125}I$ was used, or by colour change if enzyme conjugated antibodies had been employed.

The assay techniques described above will all initially demonstrate the presence of the Herpes group virus under investigation in a qualitative manner but by using techniques known per se, each of the assays described above can be made a quantitative assay by the use of conventional calibration techniques.

The method of the present invention may also be used to detect the presence of the antibody to a virus of the Herpes group. This method involves removing beta$_2$m from the serum or other clinical material being tested for specific antibodies to Herpes group virus e.g. CMV, thus preventing competitive binding between beta$_2$m and specific antibody present in the same specimen for the viral antigenic sites. It is considered that this will also aid in detecting antibodies to viral antigens to which beta$_2$m does not itself bind since these may also be masked due to steric hindrance by binding of beta$_2$m to other viral antigens on the solid phase.

Beta2m can be removed from clinical specimens being tested for antibodies to CMV by filtration through membranes which allow passage of beta$_2$m (either free or HLA bound) but retain immunoglobulin molecules. Alternatively polyclonal or monoclonal antibodies to beta$_2$m can be used to absorb beta$_2$m from the specimen. Such antibodies can be bound to a solid phase such as an affinity column, sepharose beads or other solid supports and the specimen to be tested passed over or mixed with this solid phase. After such absorption of contaminating beta$_2$m the specimen can then be tested for specific antibodies to CMV by conventional methods.

However, antibody detection assays will normally involve the use of an insolubilised virus antigen and, in accordance with the present invention, such antigen must be prepared free from beta$_2$m to allow optimum binding of the antibody.

An antigen preparation of a virus of the Herpes group is normally prepared by infecting cells such as human embryo lung fibroblasts in vitro in cell culture or in the case of EBV from EBV transformed lymphoblastoid cells. Such cells are grown in defined culture media which in the case of fibroblast cells could be minimum essential media (MEM) with the addition of glutamine, antibiotics and foetal calf serum. Foetal calf serum contains beta$_2$m which interferes with the binding of specific antibody to the virus. Other sources of serum (horse, human etc.) would also contain beta$_2$m and be subject to the same problems. Thus our preferred method involves the growing of cells for antigen preparation in media devoid of serum or beta$_2$m contamination either by removing the beta$_2$m from the serum added to the culture media or using a serum substitute such as Ultroser-G (LKB). We have found that a 1:1 mixture of MEM:HAM defined media supplemented with glutamine, antibiotics and 2% Ultroser-G is an example of a suitable culture medium for growing cells for virus antigen preparation. Cells can then be infected with the virus and virus antigen prepared by the usual routine methods.

Control antigen from uninfected cells should also be prepared free from beta$_2$m in the same manner as for the virus antigen preparation.

The presence of specific antiviral antibody in clinical specimens can then be detected by a number of existing techniques. One preferred method involves an enzyme-linked immunoabsorbent assay (ELISA) which permits an immunochemical identification. In this assay the virus antigen or control antigen (free from contamination with beta$_2$m) can be bound to solid supports such as tubes, microtitre plates or beads. The specimen to be tested for antiviral antibody can then be incubated with the virus/control antigen bound to the solid support. The unbound material is washed away and the bound antiviral antibody detected by a suitable antibody (either monoclonal or polyclonal) directed against the species from which the specimen had been obtained (i.e. against human antibody in specimens from patients). The binding of this second antibody can be detected in one of two ways: (1) if this antibody has been directly conjugated to an enzyme, by the addition of a suitable substrate and measurement of optical density change or (2) by the further addition of an enzyme conjugated antibody directed against the species in which the former antibody had been raised.

Other methods of detecting the presence of antiviral antibody which are in principle identical to that of the ELISA just mentioned can be used. For example it is possible to utilise either antibodies labelled with $^{125}$I (radioimmunoassay) or fluorescent conjugates (immunofluorescence) instead of the enzyme conjugated antibodies used in the ELISA. Thus the final detection is by $\gamma$ counting or by the observation of fluorescence under the UV microscope.

Variations of these basic methods include reverse assays in which the antibody is first 'captured' using monoclonal or polyclonal antibodies to immunoglobulin sub-classes on the solid phase to bind all antibodies of that isotype from the clinical specimen, followed by the addition of the specific viral antigen. Again this viral antigen should be free from contamination with beta$_2$m. Detection is then by addition of either directly labelled specific antiviral antibody or a two-step procedure with antiviral antibody then a labelled second antibody. The choice of enzyme, radioactive or fluorescent labelled antibodies determines the final readout as outlined above for the direct assays.

Other less-sensitive conventional techniques for the detection of antiviral antibodies can also be used such as complement fixation and passive haemagglutination inhibition, provided that the virus antigen preparation is free from beta$_2$m.

The present invention also provides a method of diagnosing whether a human or animal subject is infected with a virus of the Herpes group which comprises taking from the subject a body fluid sample and detecting the presence or absence in the sample of the virus or the corresponding antibody against the virus using a method as described above for the detection of the antigen or antibody. Preferably the body fluid is a urine, blood, saliva or bronchoalveolar lavage fluid sample.

The invention will now be described in further detail in the following Experiments and Examples. Experiment 1 describes the ELISA method which is used in subsequent Experiments and Examples. Experiment 2 shows that when ELISA is used in a known manner to test clinical samples, unreliable results are obtained. Experiments 3 to 6 demonstrate and identify the presence of the inhibitory substance in clinical samples. Experiments 7 and 8 demonstrate the ability of CMV grown in various ways to bind beta$_2$m.

Example 1 illustrates that embodiment of the invention where detectability of CMV is improved by acidification and incubation of the sample. Examples 2 and 3 illustrate that embodiment of the invention involving capture of the CMV using the presence of the inhibitor followed by detection of the viral protein. Example 4 illustrates that embodiment of the invention involving capture of the CMV using the presence of the inhibitor followed by the detection of the viral DNA.

While these Examples illustrate the technique in relation to CMV, it will be appreciated by those skilled in the art that similar techniques can be used in an exactly analogous manner with the other Herpes group viruses, all of which develop a surrounding envelope derived from their host cells.

EXPERIMENT NO. 1

ELISA Method

Optimal concentrations of all reagents were determined by chessboard titrations. All washing procedures were carried out five times with phosphate buffered saline (PBS) containing 0.05% Tween 20. The wells of flat bottomed microelisa plates (Immulon, Dynatech) were coated with 100μl of ascites fluid containing CMV-specific monoclonal antibody CH16 (Pereira et al 1982) diluted 1/1500 in 0.1M carbonate buffer (pH 9.6). The monoclonal antibody was allowed to adsorb to the plates at 4° C. for at least 20 hours before use. After washing, remaining protein binding sites in the wells were blocked with 1% bovine serum albumin (BSA) in PBS for 90 minutes at room temperature. After washing, four wells were incubated at 37° C. for 90 minutes with 100 μl of each specimen. As controls, at least one known infected and three known uninfected samples were applied to each plate. The plates were washed and 100 μl of a 1/100 dilution of human serum known to contain CMV IgG antibodies detected by radioimmunoassay was applied to each sample in duplicate. To control for non-specific binding an identical concentration of human serum lacking CMV IgG antibodies was added to the remaining two wells. The plates were then washed and 100 μl of a 1/1000 dilution of alkaline phosphatase labelled affinity-purified goat anti-human IgG (TAGO) in 1% BSA PBS was added. After a one hour incubation at 37° C. and another wash, 100 μl of a 1 mg/ml solution of P-nitrophenyl phosphate (Sigma) in 10% diethanolamine (pH 9.8) was added and allowed to react at 37° C. for 30 minutes. Colourimetric conversion of the substrate was measured in a microplate spectrophotometer at 410nm wavelength (Flow Multiskan).

To calculate results, the mean Absorbance (Abs) reading of samples with non-immune serum was subtracted from the mean ΔAbs of those incubated with immune serum to give a specific value for a sample (ΔAbs). The mean Abs of the negative controls was also calculated. In the case of clinical samples a specimen was considered positive if its ΔAbs was greater than the mean +2SD of the ΔAbs of the negative control samples. In order to compare the results obtained in different assays, an absorbance ratio was calculated by dividing the mean ΔAbs of the clinical sample by the mean +2SDΔAbs of the negative control samples. Thus, any sample with an absorbance ratio of greater than 1.0 had given a ΔAbs greater than the mean +2SD of the internal controls tested in the same assay.

Figure 1:
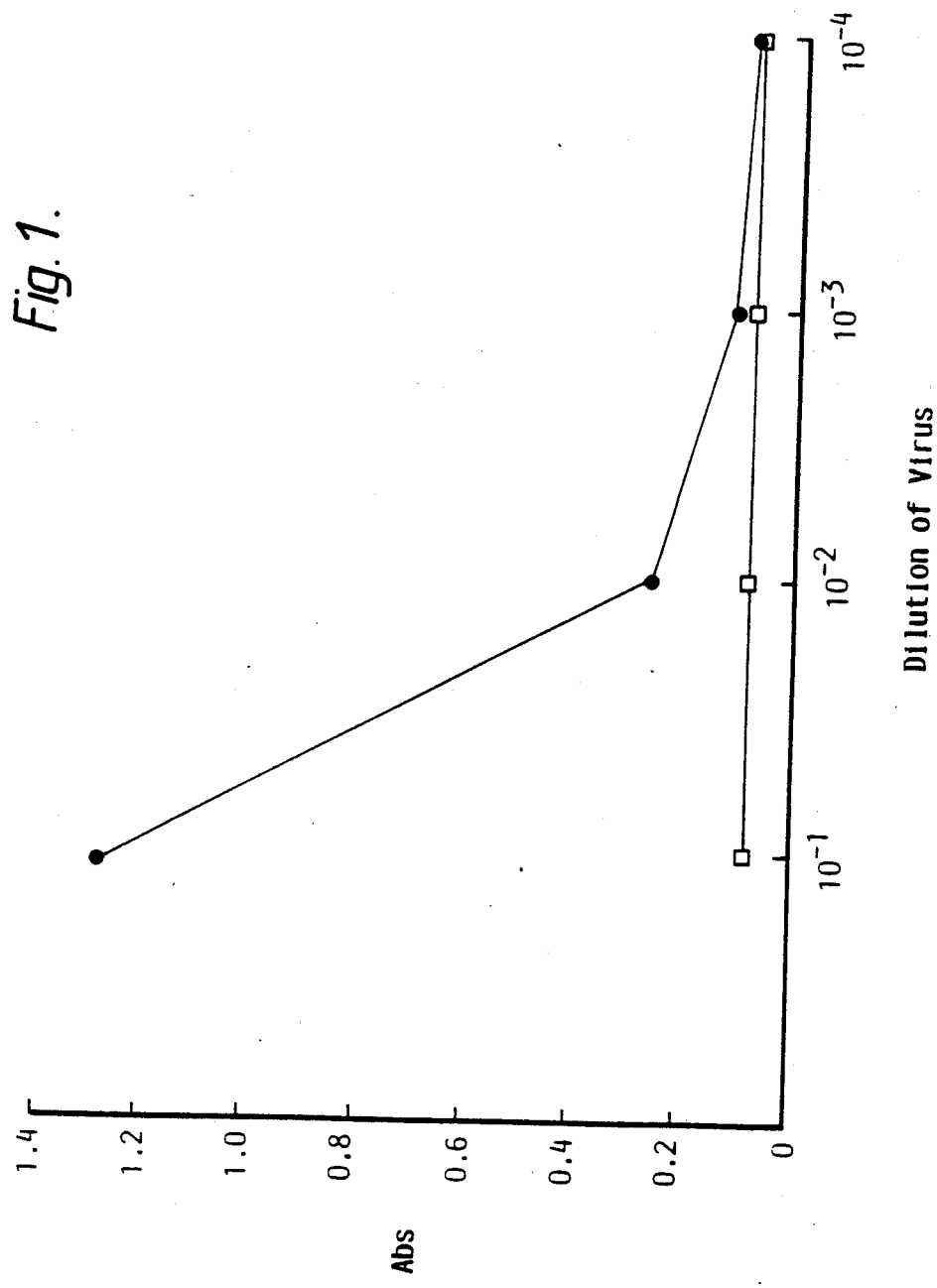
FIG. 1 illustrates detection of tissue culture grown CMV in the ELISA.
Figure 2:
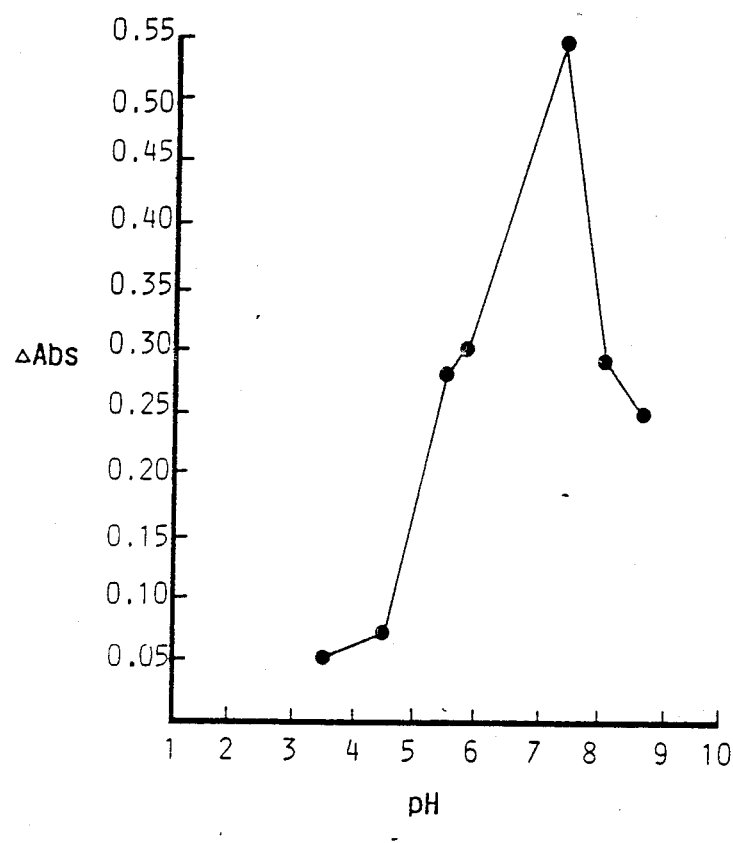
FIG. 2 shows the effect of pH on the detection of tissue culture grown CMV in the ELISA.

A laboratory strain (AD169) of CMV was used to evaluate the ELISA assay. Human embryonic lung (HEL) cells or human foreskin fibroblasts were grown in MEM (GIBCO) with 2% fetal bovine serum (FLOW) and infected with AD169. When virus cytopathic effect was extensive the supernatant fluid was harvested and clarified at 2000g for five minutes. This tissue culture grown virus was titrated in HEL cells and assayed using the ELISA. The ELISA was capable of detecting the tissue culture virus down to $10^{2.3}$ TCID units/ml (FIG. 1). Furthermore it was highly specific for CMV; supernatance from HEL cell cultures infected with herpes simplex virus or varicella zoster virus gave negative ELISA results. Detection of tissue culture CMV in the ELISA was found to be optimal at pH 7.3, at higher or lower pH values the sensitivity was greatly reduced (FIG. 2).

FIG. 1 shows detection of tissue culture grown CMV strain AD169 in the ELISA (●), supernatants from uninfected cells are shown (□). The virus stock used had a titre of $10^{-4.3}TCID_{50}$ units. FIG. 2 shows effect of pH on the detection of tissue culture grown CMV strain AD169 in the ELISA.

EXPERIMENT NO. 2

The ELISA system in Experiment 1 described above was applied to the detection of CMV in clinical specimens. The ELISA was unable to detect CMV in 46/46 fresh (<24 hours) urine specimens known to contain the virus as detected by conventional cell culture techniques (Table 1). Furthermore the ELISA result was variable, storage of urine specimens at 4° C. for varying periods often resulted in a positive ELISA result in a specimen previously negative in the ELISA (Table 1). The alteration in the detectability of CMV in urine as a function of time of storage at 4° C. can be seen in FIG. 3. Thus when applied to clinical specimens the ELISA was found to be both insensitive and variable. Urine samples range in pH from 4.0 to 10.0 and therefore in an attempt to increase sensitivity, specimens were adjusted to pH 7.3 as this pH was found to be optimal in the ELISA (see ELISA method, FIG. 2). However, such adjustment failed to increase detectability of CMV in urine specimens by the ELISA.

Figure 3:
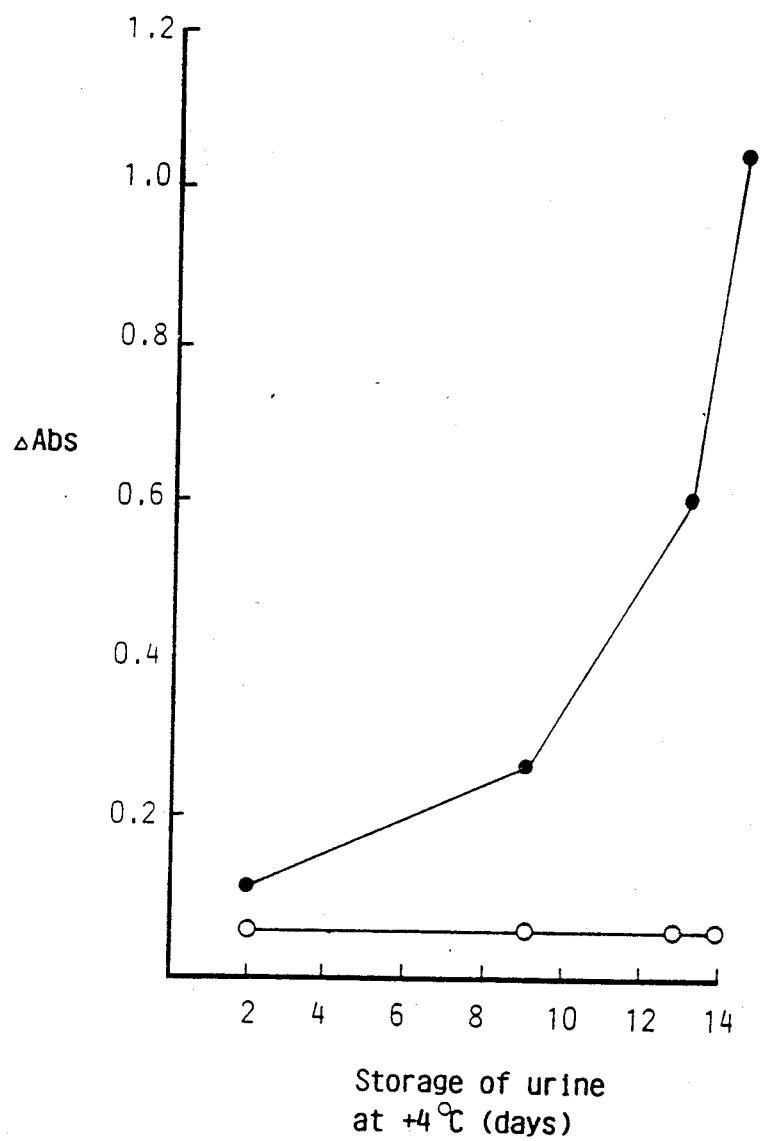
FIG. 3 shows the effect of storage at 4° C. on the detection of CMV in a urine sample by the ELISA.

FIG. 3 shows the effect of storage at 4° C. on the detection of CMV in a urine sample by the ELISA. ΔAbsorbance of the urine sample known to contain CMV is shown (●) and of an uninfected urine (0).

TABLE 1

ELISA results obtained by testing urine samples fresh and again following storage at 4° C. for two weeks

| CELL CULTURE RESULT | ELISA RESULT ON URINE: | | | |
|---|---|---|---|---|
| | FRESH | | STORED | |
| | + | − | + | − |
| + | 0 | 46 | 35 | 11 |

EXPERIMENT NO. 3

Uninfected urine from normal individuals contains a substance(s) with molecular weight <25,000 daltons which inhibits the detection of tissue culture grown CMV in the ELISA.

Figure 4:
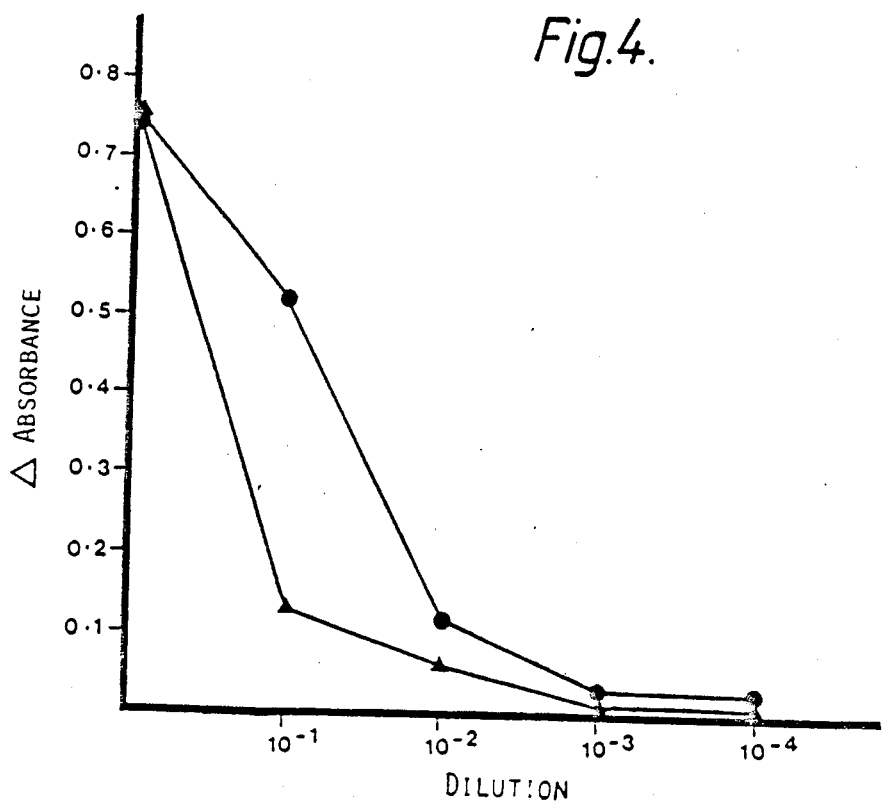
FIG. 4 shows the inhibitory effect of urine from a normal healthy CMV seronegative individual on the detection of tissue culture grown CMV in the ELISA.

The pH of uninfected urine specimens was measured and 0.1M citrate buffers were made up at the same pH for use as controls. 0.1 volume of tissue culture grown virus (prepared as described in ELISA method) was added to the urine specimen, or to citrate buffer at the same pH and serially diluted in PBS. 100 μl of each dilution was added to the ELISA plates as per specimens in the ELISA protocol and the ELISA performed as described. As can be seen in FIG. 4, the presence of normal uninfected urine decreased the ability to detect tissue culture grown virus in the ELISA when compared to a citrate buffer at the same pH.

The inhibitory effect of the normal uninfected urine was still observed after passage of the urine through an amicon filter (CF25) with an exclusion of molecules with molecular weight ≧25,000 daltons. Urine specimens were placed in the amicon filter cone and spun at 850g for 15 minutes. The filtrate was added to tissue culture grown virus and assayed in the ELISA as just described. The concentrate was reconstituted to the original concentration of the urine and assayed as per the filtrate. Table 2 shows that the inhibitory activity was solely found in the filtrate and therefore the inhibitor(s) must have a molecular weight <25,000 daltons.

FIG. 4 shows the inhibitory effect of urine from a normal healthy CMV seronegative individual on the detection of tissue culture grown CMV in the ELISA. Virus plus urine is shown (▲) and in citrate buffer at the same pH as the urine (●). Each of latter samples were serially diluted in PBS and assayed for CMV in the ELISA.

TABLE 2

Inhibitory effect of urine on the detection of tissue culture grown virus in the ELISA after passage of the urine through an amicon filter with exclusion of molecular weight ≧ 25,000 daltons.

| | Absorbance | % Inhibition |
|---|---|---|
| whole urine | 0.306 | 34% |
| filtration mwt <25,000 | 0.276 | 40% |
| concentrate mwt ≧25,000 | 0.511 | — |
| PBS control | 0.463 | — |

EXPERIMENT NO. 4

The inhibitory substance in urine which reduces the detectability of tissue culture grown CMV in the ELISA co-elutes on a Sephadex G50 column with beta2 microglobulin (beta$_2$m)

Uninfected urine from a renal transplant patient was concentrated using polyethylene glycol and 23/32 visking tubing. The concentrate was then passed through an amicon cone (G250) and 0.5ml of the filtrate (known to contain the inhibitory activity in the ELISA—see Experiment 3) was loaded onto a Sephadex G50 (Pharmacia) column (28 cm×1.3 cm). Fractions were eluted in 0.02M Tris/0.15M NaCl buffer at pH 7. Twenty 30-drop (approximately 3 ml) fractions were collected and stored at −20° C. until tested. All fractions were assayed for their ability to inhibit the detection of tissue culture grown CMV strain AD 169 in the ELISA as in Experiment 3.

Figure 5:
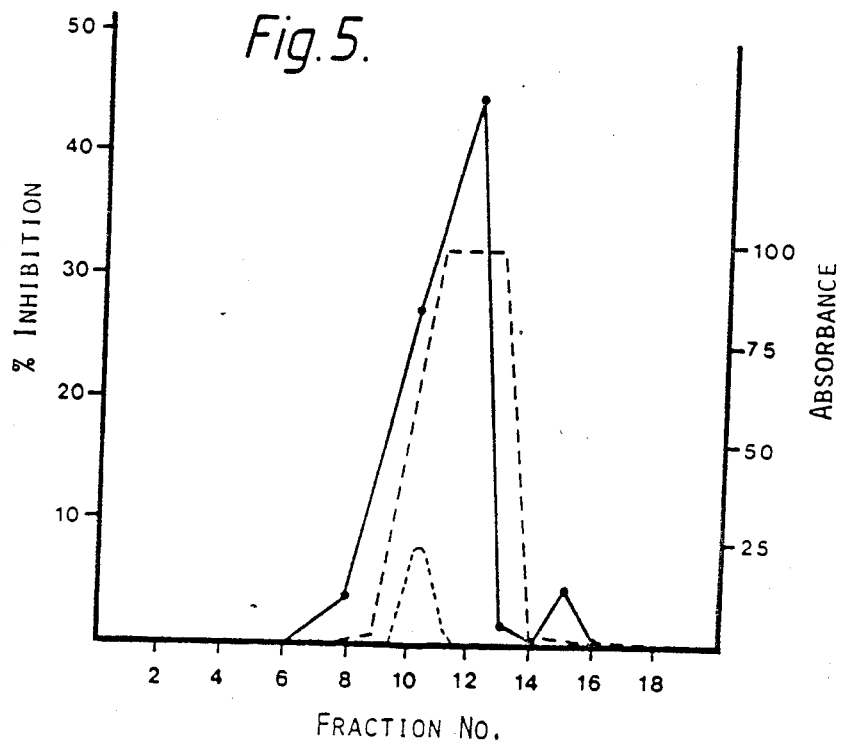
FIG. 5 shows the peak of protein and the peak of inhibitory activity of urine on the detection of CMV in the ELISA after elution from a Sephadex G50 column.

FIG. 5 shows that the peak of protein (absorbance at 280nm), fractions 10 to 13, coincides with the peak of inhibitory activity in the ELISA, fractions 9 to 12. Purified beta$_2$m (Serotec, OAE 02A) was passed over the same column and was found to elute at fractions 11–12. Thus the inhibitory activity present in the urine of normal seronegative individuals which inhibits the detection of tissue culture grown CMV in the ELISA co-elutes with beta$_2$m.

FIG. 5 shows the peak of protein and the peak of inhibitory activity of urine on the detection of CMV in the ELISA after elution from a Sephadex G50 column. The absorbance at 280nm of the fractions are shown—— —and the % inhibition in the ELISA as ●—● . The absorbance at 280 nm of purified beta$_2$m passed over the same column is shown ---- .

EXPERIMENT NO. 5

Cytomegalovirus purified directly from urine has beta$_2$m bound to its envelope as demonstrated by western blotting techniques.

Urine from patients excreting CMV was clarified by centrifugation at 1,500g for 15 minutes and the clarified urine concentrated using an Amicon stirred cell concentrator with YM100 membranes. Concentrated urine was centrifuged through a potassium tartrate/glycerol negative viscosity/positive density gradient (Talbot & Almeida, 1977) at 400,000g for 45 minutes. The visible virus band was harvested and the viral proteins separated by electrophoresis in 8 to 12% gradient polyacrylamide gels in the presence of 0.1% SDS (Laemmli, 1970). The separated proteins were transferred to nitrocellulose membranes using 25 mM Tris HCL, 192 mM Glycine pH8.3 with 20% methanol (Towbin et al 1979). Non-specific protein binding sites were blocked by treating the filters with 2% rabbit serum, 3% BSA, 0.2% Tween 20, 0.2% sodium azide in PBS (Buffer A) for 3 hrs at 4° C. The membranes were incubated with 5ml of monoclonal antibody specific for human beta$_2$m (SRL-3, Serotec) diluted 1/500 in buffer A for 12 hrs at 4° C. After 4 washes in 50 mM Tris-Cl, 0.9% (w/v) Na Cl, 1 mM EDTA, 0.25% BSA, 0.05% Tween -20, pH7.4 (Buffer B), the membranes were treated with $^{125}$I-labelled sheep anti-mouse immunoglobulin (Amersham) at 10$^5$ counts per minute/ml in Buffer A for 12 hrs at 4° C. Unbound antibody was removed by repeated washing with buffer B, followed by drying and autoradiography.

Figure 6:
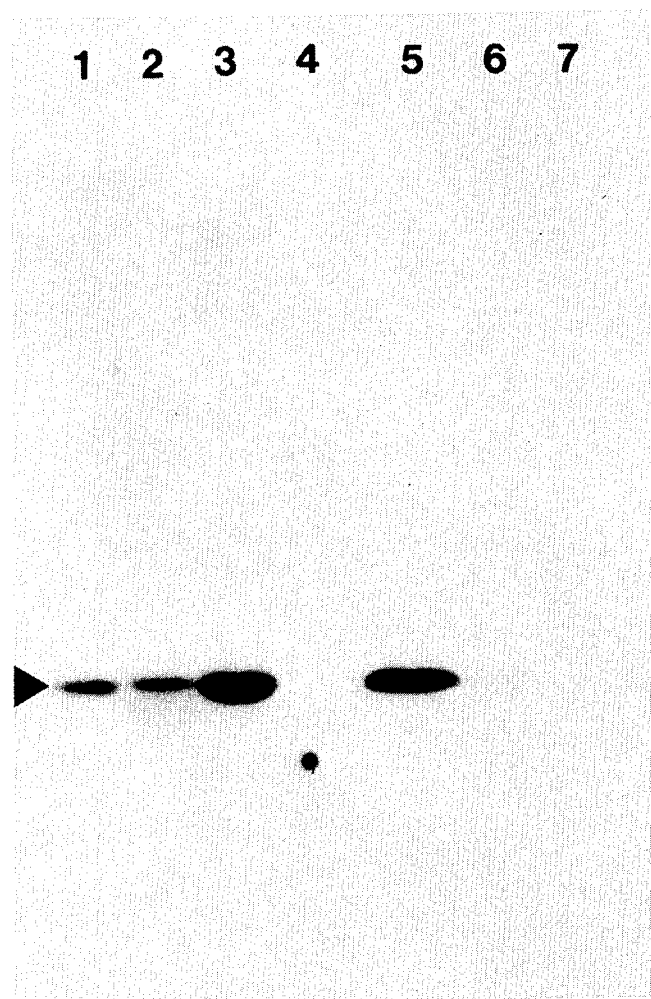
FIG. 6 is an autoradiograph of a Western blot showing the presence of beta$_2$m in purified preparations of urinary CMV.

The autoradiograph of a western blot of separated viral proteins shows the presence of a beta$_2$m band in the virus preparations from five different urine specimens (FIG. 6). In contrast, such a band was not seen with cell culture grown CMV strain AD169, or in the ultracentrifuged pellet of urine from a CMV seronegative individual.

Figure 7:
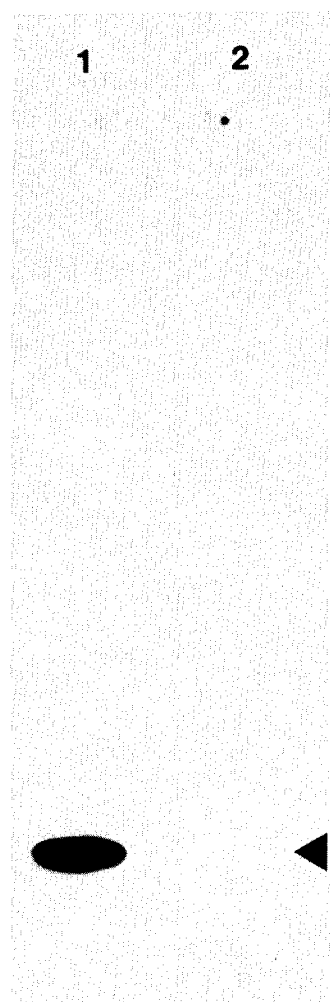
FIG. 7 is an autoradiograph of a Western blot showing that beta$_2$m is associated with the envelope of urinary CMV.

The envelope of urinary CMV purified as above was extracted with 10 mM Tris-HCL, 1 mM CaCl$_2$, 0.15M NaCl, 1% Triton X-100, 2 mM phenylmethylsulphonyl fluoride, 1% ethanol at pH7.3 and treatment with ultrasound (2 bursts of 30 seconds at 0° C.) in an ultrasonic water bath (Farrar et al, 1984). After 20 minutes at 0° C., the suspension was ultracentrifuged at 50,000g for 40 minutes at 4° C. Pelleted material was resuspended in PBS and analysed with the supernatant. An autoradiograph of a western blot of the triton soluble and triton insoluble fractions (FIG. 7) shows that such treatment of urinary CMV with triton to solubilise the envelope components resulted in the loss of the beta$_2$m band in the insoluble fraction, whilst beta$_2$m was present in the triton soluble fraction, thus indicating that the beta$_2$m was associated with viral envelope of urinary CMV.

FIG. 6

Autoradiograph of a western blot of separated viral proteins showing the presence of beta$_2$m in CMV preparations from five different urine specimens (tracks, 1, 2, 3, 5 and 6). The viral proteins were separated in an 8–12% gradient SDS polyacrylamide gel, transferred to nitrocellulose filters and a mouse monoclonal antibody to human beta$_2$m (SRL-3) used for the detection. The arrow indicates the position of purified human beta$_2$m on this filter. No beta$_2$m band was seen in track 4 which was loaded with cell culture grown CMV strain AD169.

FIG. 7

Autoradiograph of a western blot showing loss of beta$_2$m from urinary CMV after triton extraction of the viral envelope. The triton soluble viral protein fraction separated in track 1 shows the presence of a beta$_2$m band, as detected with the monoclonal antibody SRL/3 specific for beta$_2$m. The triton insoluble viral proteins separated in track 2 do not contain beta$_2$m. The arrow indicates the position of purified beta$_2$m on this filter.

EXPERIMENT 6

Purified beta$_2$m at physiologic concentrations inhibits the detection of tissue culture grown CMV strain AD169 in the ELISA.

Cell culture grown CMV strain AD169 prepared as in Experiment 1 was ultracentrifuged at 90,000g for 1 hr. Increasing concentrations of purified human beta$_2$m (Serotec) from 0.006 µg/ml to 0.1 µg/ml (final concentration) in phosphate-buffered saline were added to either the resuspended pellet containing CMV virions or the supernatant containing the soluble viral glycoproteins. The inhibitory activity of another urinary protein of low molecular weight, lysozyme, was assayed in a similar manner. Each sample was then assayed for CMV by ELISA as in Experiment 1 and results were expressed as percentage inhibition.

Figure 8:
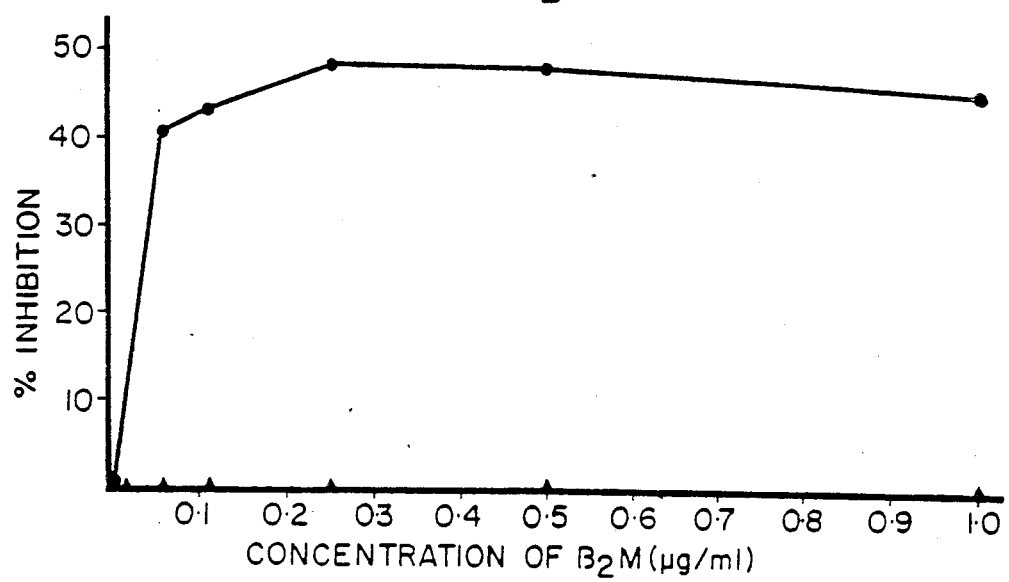
FIG. 8 shows the effect of the addition of increasing concentrations of beta$_2$m on the detection of tissue culture grown CMV in the ELISA.

At concentrations at or above 0.05 µg/ml, the addition of beta$_2$m inhibited the ELISA detection of CMV virions (FIG. 8). In contrast, although soluble viral glycoproteins could be detected in the ELISA, this reaction could not be inhibited by the addition of beta$_2$m (FIG. 8). Conversely, the addition of another urinary protein, lysozyme, of low molecular weight (14,400 daltons) had no inhibitory effect on the ELISA detection of CMV (results not shown).

In order to show that the beta$_2$m was binding to the virus and not to the capture antibody the above experiment was modified. Beta2m was added either to the capture antibody on the ELISA plate (in 10 µl in PBS) followed by 3 washing steps and then virus was added, or beta$_2$m was added to the virus preparation and the mixture then added to the ELISA plate. The virus preparation was not separated into virions and soluble glycoproteins in the latter experiment. Table 3 shows that beta$_2$m only inhibited detection of the tissue culture grown virus if added to the virus preparation and not if added to the capture antibody. Thus beta$_2$m was inhibiting detection by interacting with the virus and not the antiviral antibody.

FIG. 8

The effect of the addition of purified beta$_2$m on the detection of cell culture grown CMV strain AD169 in the ELISA. The inhibitory effect of increasing concentrations of beta$_2$m on the ELISA detection of CMV virions (●) and of soluble viral glycoproteins are (▲) are shown. The range of beta$_2$m excreted in the urine of normal healthy individuals is 0.05–0.07 µg/ml but in patients with severe renal tubular dysfunction this can be appreciably higher.

TABLE 3

Comparison of the addition of purified beta$_2$m to the monoclonal capture or to the virus preparation, on the detection of tissue culture grown CMV in the ELISA.

| Addition of beta$_2$m to | | | |
|---|---|---|---|
| Capture Antibody | Virus Preparation | Elisa Result (absorbance) | % Inhibition |
| − | − | 0.667 | |
| + | − | 0.601 | 9.9% |
| − | + | 0.299 | 55.2% |

EXPERIMENT NO. 7

CMV grown in vitro in cell culture binds beta$_2$m when this protein is present in the culture medium.

Human foreskin fibroblasts were grown in serum free MEM with a serum substitute Ultraser G (LKB) at 2% concentration. These cells were infected with CMV strain AD169 in the presence or absence of beta$_2$m at 2 µg/ml in the culture fluid. The virus was harvested from the culture fluid and purified by ultracentrifugation through potassium tartrate/glycerol gradients at 400,000g for 45 mins. (Talbot & Almeida, 1977) and the proteins separated by electrophoresis in an 8–12% SDS polyacrylamide gel in the presence of 0.1% SDS according to Laemmli 1970. A protein band of molecular mass 11–12,000 daltons was seen in the track loaded with CMV strain AD169 grown in medium with added beta$_2$m.

The proteins were transferred to nitrocellulose membranes using 25 mM Tris-HCl, 192 mM glycine pH8.3 with 20% methanol according to the method of Towbin et al, 1979. Non-specific protein binding sites were blocked by treating the filters with Buffer A (see Experiment 5) for 3 hours at 4° C. The membranes were incubated with 5 ml of monoclonal antibody specific for human beta$_2$m (SRL-3, Serotec) diluted 1/500 in Buffer A for 12 hours at 4° C. after 4 washes in Buffer B (see Experiment 5). The presence of specific bands was detected by treating the membranes with $^{125}$I-labelled sheep anti-mouse immunoglobulin (Amersham) at $10^5$ counts per minute/ml in Buffer A for 12 hours at 4° C. Unbound antibody was removed by repeated washing with Buffer B and after drying, the specific bands were detected by autoradiography.

Figure 9:
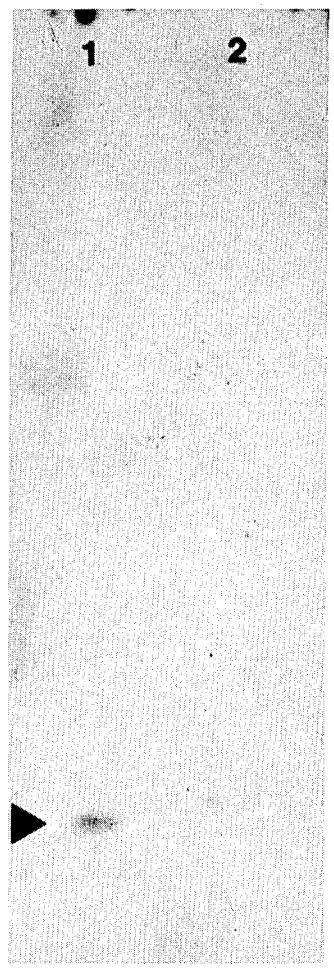
FIG. 9 is an autoradiograph of a Western blot showing that CMV can bind beta$_2$m when grown in its presence in cell culture.

The autoradiograph of a western blot of the separated CMV proteins (FIG. 9) showed a single band in the virus preparation grown in serum free medium to which purified human beta$_2$m was added. This band was at the same position as that seen when purified human beta$_2$m was run on the same gel. Thus CMV grown in vitro can acquire human beta$_2$m when it is present in the cell culture fluid.

FIG. 9

Autoradiograph of a western blot of separated CMV strain (AD169) proteins detected with a murine monoclonal antibody to human beta$_2$m (SRL-3). The virus was grown in either serum free medium alone (track 2) or with the addition of purified human beta$_2$m at 2 g/ml-1 (track 1). The arrow indicates the position of beta$_2$m on this filter.

EXPERIMENT NO. 8

Beta$_2$m is acquired by CMV strain AD169 from cell culture fluids after release from cells.

Figure 10:
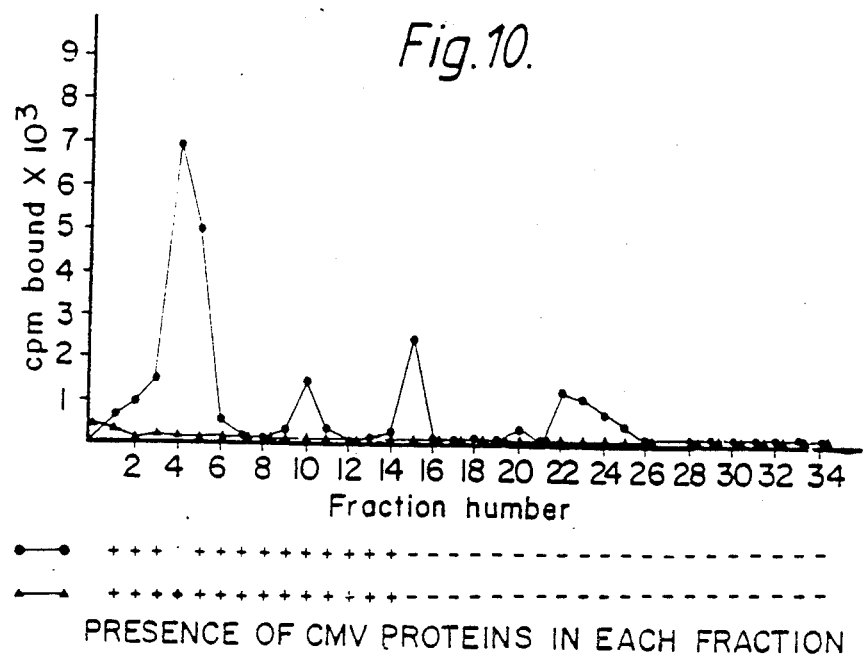
FIG. 10 shows the acquisition of labelled beta$_2$m by extracellular CMV strain AD169 from cell culture medium.

Human foreskin fibroblasts were grown in MEM with 2% ultroser G (LKB) and, after adsorption of AD169 for one hour, medium containing $I^{125}$-labelled human beta$_2$m was added at 2 μg/ml. The beta$_2$m (Serotec) was iodinated with iodogen (Fraker et al 1978) and unincorporated isotope was removed by gel filtration through Sephadex G50 (Pharmacia). Extracellular virus was purified from the supernatant by ultracentrifugation through a potassium tartrate/glycerol gradient at 400,000g for 45 mins. (Talbot and Almeida 1977). Intracellular virus was harvested by scraping off the cells, freezing and thawing three times, followed by ultrasonic disruption (2 bursts of 30 seconds in an ultrasonic water bath). After clarification at 1,500g for 30 mins. the intracellular virus was gradient purified as for the extracellular virus. Fractions from the gradient were counted for radioactivity and each fraction was also analysed for the presence of CMV proteins by immunoblotting as follows: 5 μl of fraction was spotted onto nitrocellulose and air dried. The filter was quenched in Buffer A (see Experiment 5) at room temperature for 30 mins. and washed in Tris buffered saline (TBS) (0.01 M Tris-HCE 0.15 m NaCl, pH 7.5) four times. The filter was then incubated with a pool of CMV specific monoclonal antibodies (CH33, CH45 and CH92) (Pereira et al 1982) diluted in Buffer A at 37° C. for 2 hrs. The filters were washed 4 times in TBS and incubated with biotin anti-mouse immunoglobulin (Sigma) in Buffer A for 2 hrs. at 37° C. The filters were washed 4 times with TBS and incubated with horseradish peroxidase-avidin (Sigma) in Buffer A for 2 hrs. at 37° C. Finally, the filters were washed 4 times with TBS and incubated with diaminobenzedine (DAB) (50mg DAB per 100ml 0.05M Tris-Cl pH 8.3 plus the addition prior to use of 0.167 ml of 30% $H_2O_2$) until the colour reaction developed. The filters were then washed in distilled water and air dried. In the extracellular virus preparation the peak of radioactivity coincided with the visible virus band and with the fractions containing viral proteins (FIG. 10). In contrast, whilst the intracellular virus had a similar visible band on the gradient and had fractions containing viral proteins by immunoblotting, these fractions were not radiolabelled (FIG. 10). Thus CMV strain AD169 had acquired the radiolabelled beta$_2$m from the culture fluid, during or after release from cells.

FIG. 10

Acquisition of $^{125}$I-labelled beta$_2$m by extracellular CMV strain AD169 from cell culture medium. Cells were grown in serum free medium and after infection with AD169, $^{125}$I-labelled beta$_2$m was added at $10^5$cpm/ml. Intracellular and extracellular virus was purified on potassium tartrate/glycerol gradients and the radioactivities incorporated in each fraction is shown for the two virus preparations by ○ and ● respectively. The fractions containing the virus, as determined by immunoblotting using CMV monoclonal antibodies are shown (+).

EXAMPLE 1

The inhibitory activity of urine on the detection of CMV in the ELISA was lost if the urine was acidified and incubated at 37° C. for 1 hour.

Figure 11:
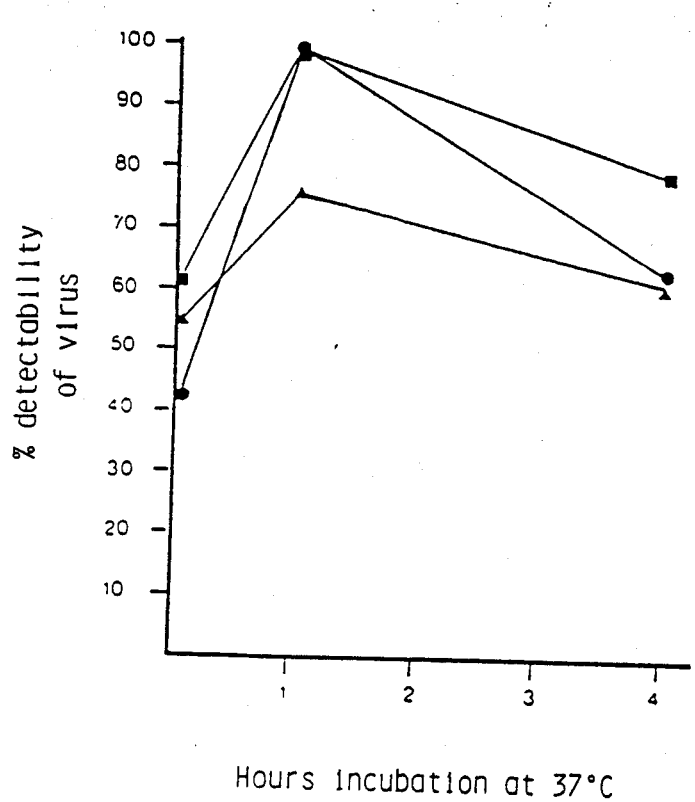
FIG. 11 shows the effect of incubation at 37° C. and pH on the ability of urine from a normal CMV seronegative individual to inhibit the detection of CMV in the ELISA.

Urine from a normal CMV seronegative individual was adjusted with 1M NaOH or 1M HCl to give pH values of 8.4, 6.45 or 4.85. Aliquots of each were incubated at 37° C. for 0, 1 or 4 hours or held at 4° C. Samples were then re-adjusted to pH 7.3 by the addition of an equal volume of 0.1M $PO_4$ buffer pH 7.3 Samples were stored at −20° C. until assayed. Each sample was added to tissue culture grown CMV strain AD169 and assayed in the ELISA. FIG. 11 shows the effect of incubation at 37° C. and pH on the ability of urine from a normal CMV seronegative individual to inhibit the detection of CMV in the ELISA.

The urine sample was adjusted to pH 8.4 (▲), 6.5 (●) or 4.85 (■) and incubated for 0, 1 or 4 hours at 37° C. before being added to tissue culture grown in CMV strain AD 169 in the ELISA. The figure shows the % of CMV detectable compared to the control with PBS instead of urine added. FIG. 11 shows that the inhibitory effect of urine was lost after incubation at 37° C. at acidic pH, either 6.45 or 4.85. It is known that urine contains an enzyme(s) capable of degrading beta$_2$m which is active at acid pH (Eurin et al 1972, Davey et al 1982). Incubation for 4 hours at 37° C. was accompanied by a re-emergence of inhibitory activity. It is not known whether certain degradation products of beta$_2$m are capable of binding to the virus.

EXAMPLE 2

Cytomegalovirus can be immunoprecipitated from urine by monoclonal antibodies specific for beta$_2$m, as demonstrated by the presence of CMV proteins in the immunoprecipitates.

Urine from patients excreting CMV was clarified by centrifugation at 1,500g for 15 minutes and the clarified urine concentrated using an Amicon stirred cell concentrator with YM100 membranes. 25 μl of concentrated urine containing CMV was pretreated with 10 μl of 10% BSA in PBS for 1 hour at 4° C., and non-specific immune complexes were removed by adsorption to protein A-sepharose (Pharmacia), 20 μl of a 30% (V/V) suspension for 1 hour at 4° C. followed by centrifugation in a microcentrifuge (MSE) for five minutes. The pellet was washed twice 1% Triton X-100 in PBS pH7.4 and the supernatants pooled with the first supernatant. The supernatant pool was incubated with 40 μl of diluted antibody for 12 hours at 4° C. Six monoclonal antibodies specific for beta$_2$m were used, namely BBM.1 (American Type Culture Collection hybridoma HB28), HLA ABC.M2, BIG 6, SRL-3 (Serotec), 26/114 HLK, FMC 16 (Sera-Lab) and C23 (gift from Dr. A. Sanderson).

The specific immune complexes were adsorbed to Protein A-Sepharose as described above. The beads were washed twice in 1% Triton X-100 in PBS pH7.3 and then resuspended in 1% SDS and heated for 3 minutes at 100° C. The samples were electrophoresed in 8 to 12% gradient polyacrylamide gels in the presence of 0.1% SDS (Laemmli, 1970). Prestained molecular weight markers (BRL) were used. The separated proteins were electrophoretically transferred to nitrocellulose membranes using 25 mM Tris-HCL, 192 mM Glycine pH8.3 with 20% Methanol (Towbin et al 1979). Non-specific protein binding sites were blocked by treating the filters with 2% rabbit serum, 3% BSA, 0.2% Tween 20, 0.02% sodium azide in PBS (Buffer A) for 3 hours at 4° C. The membranes were incubated with 5ml of a pool of CMV specific monoclonal antibodies CH33, CH45 and CH92 (Pereira et al 1982) diluted 1/500, for 12 hours at 4° C. After 4 washes in 50 mM Tris-Cl, 0.9% (w/v) NaCl, 1mM EDTA, 0.25% BSA, 0.05% Tween 20, pH7.4 (Buffer B), the membranes were treated with $^{125}$I-labelled sheep anti-mouse immunoglobulin (Amersham) at 10$^5$cpm/ml in Buffer A for 12 hours at 4° C. Unbound antibody was removed by repeated washing with Buffer B, followed by drying and autoradiography.

Figure 12:
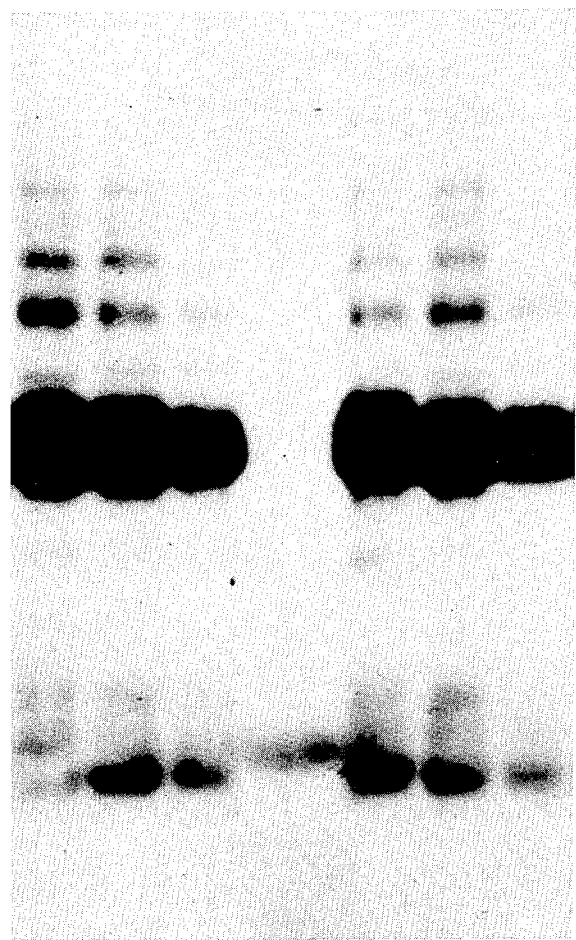
FIG. 12 is an autoradiograph showing the presence of CMV proteins by western blotting in immunoprecipitates of urinary CMV using monoclonal antibodies specific for beta$_2$m.

The results show that all six monoclonal antibodies specific for beta$_2$m were capable of immunoprecipitating CMV from urine as demonstrated by the presence of CMV proteins in the western blots of the immunoprecipitates (FIG. 12). The presence of a range of CMV glycoproteins (of 150, 130, 110, 50 and 30 kilodaltons), and an inner capsid protein in the immunoprecipitates (FIG. 12), indicates that whole viral particles and not just soluble glycoproteins were immunoprecipitated by the monoclonal antibodies against beta$_2$m.

FIG. 12

Autoradiograph showing the presence of CMV proteins by western blotting in immunoprecipitates of urinary CMV using the monoclonal antibodies BBM.1, HLA ABCm2, BIG 6, SRL-3, 26/114 HLK, FMC 16 (tracks 1, 2, 3 and 5 to 7 respectively) all specific for beta$_2$m. The immunoprecipitates were separated by electrophoresis in an 8-12% gradient SDS polyacrylamide gel, transferred to nitrocellulose filters and CMV proteins detected using a pool of CMV specific monoclonal antibodies. The arrows indicate the specific CMV proteins of molecular mass 150, 130, 110, 50 and 30 kilodaltons which can be seen in tracks 1, 2, 3 and 5 to 7. Track 4 was loaded with pre-stained molecular weight markers.

EXAMPLE 3

Cytomegalovirus can be detected in clinical specimens by capturing the virus onto a solid phase using monoclonal antibodies specific for beta$_2$m and then reacting the material so bound with a second reagent specific for CMV proteins.

A 8cm×1cm affinity chromatography column was prepared using monoclonal antibody BBM.1 (ATCC Hybridoma No HB28) specific for beta$_2$m linked to cyanogen bromide activated sepharose, 4B (Pharmacia). The column was prepared according to the manufacturer's instructions and stored in PBS with 1% sodium azide at 4° C. The monoclonal antibody used was first precipitated from ascitic fluid by ammonium sulphate and them dialysed against 0.1 M Na$_2$HCO$_3$/0.5 M NaCl pH8.3 for 72 hrs with 7-8 changes of dialysate. The column was shown to bind 17 μg purified human beta$_2$m for 200μl of gel volume.

Urine from patients excreting CMV was concentrated 500 fold by ultrafiltration using an amicon stirred cell concentrator and YM100 membranes. The column was washed at room temperature with 10 bed volumes of 50 mM TRIS, 0.5 M NaCl, 5 mM EDTA, 0.5% NP40 at pH8. Following this it was washed with 5 bed volumes of 10 mM Tris pH7.4. 1 ml of the concentrated urine was loaded onto the column. Unbound material was washed through the column with 5 bed volumes of 1M NaCl in PBS at pH7.4. The bound material was eluted with 50mM diethylamine and immediately neutralised with N-diethylmorpholin acetate. Fractions were collected and the optical density of each fraction measured. The proteins in each fraction were separated by electrophoresis in a 9-16% SDS polyacrylamide gel. In addition, each fraction was analysed for the presence of CMV proteins and beta$_2$m by a dot immunoblot assay as follows. 5 μl of the fraction was spotted onto nitrocellulose filters and air dried. Non specific binding sites were blocked with 3% BSA and 3% normal rabbit serum in PBS pH7.4 at 37° C. for 1 hour. The filters were then incubated with monoclonal antibodies specific for beta$_2$m (SRL-3, Serotec) or for CMV (CH28, CH16, CH65, CH19, Pereira et al 1982) at room temperature for 1 hour with shaking. Filters were washed 5 times for 10 minutes each with Buffer B.

The binding of the monoclonal antibodies was detected by incubation for 1 hour at room temperature with a rat monoclonal antibody specific for mouse immunoglobulin kappa chain (MRC-OX20, Serotec) which had been radiolabelled with $^{125}$I using Iodogen (Fraker et al 1977). Filters were washed 5 times for 10 minutes each as before, air dried, and the specific spots revealed by autoradiography.

Figure 13:
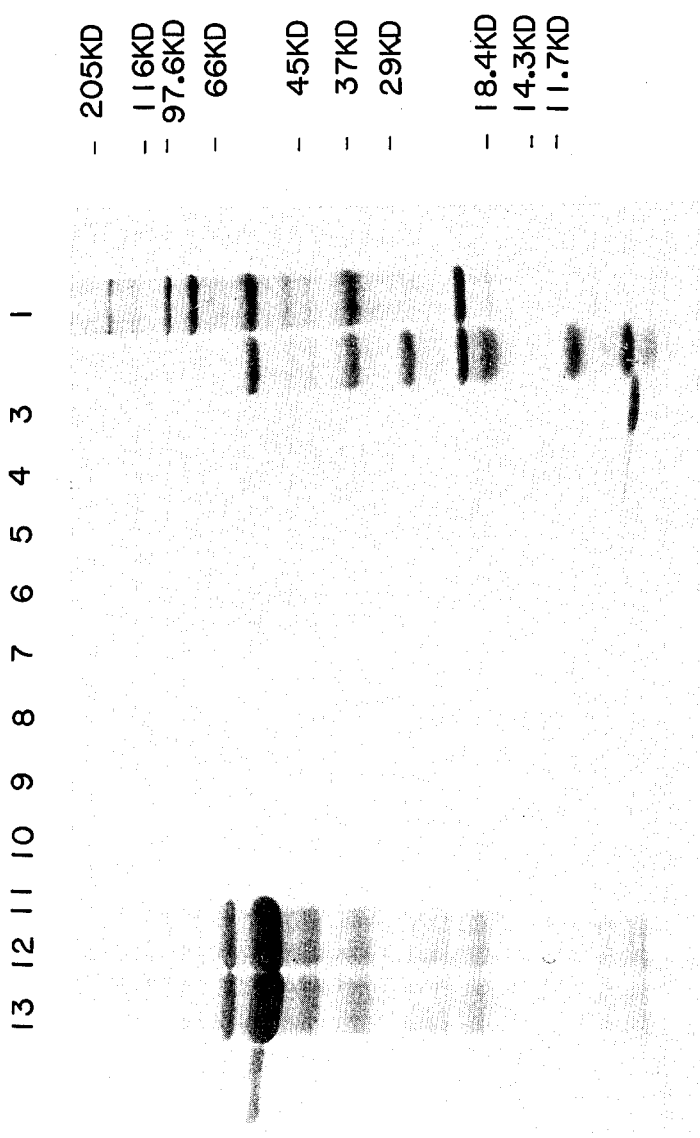
FIG. 13 shows the presence of CMV proteins in the specific eluate after passage of urine through an anti-beta$_2$m affinity column.

The results, summarized in Table 4, show that CMV proteins were detected by immunoblotting in the material eluted from an anti-beta$_2$m affinity column. The major protein peak was eluted in fraction 5 which was strongly positive for CMV by immunoblotting (Table 4). The protein profile of the fractions containing the specific eluate also demonstrated the characteristic pattern of urinary CMV proteins as can be seen in FIG. 13. The fractions containing CMV proteins also contained beta$_2$m, supporting other findings that these two entities are bound together in urine.

Thus the presence of CMV in urine can be detected by capturing the virus onto the solid phase using a monoclonal antibody specific for beta$_2$m, eluting the bound material and then probing for the presence of CMV proteins using CMV specific monoclonal antibodies.

TABLE 4

Presence of CMV in the specific eluate after passage of urine containing the virus through a beta$_2$m specific affinity column as demonstrated by immunoblotting.

| Fraction No | Official Density at 280 nm | CMV Proteins | Beta$_2$m |
|---|---|---|---|
| 1 | 0.057 | − | − |
| 2 | 0.071 | − | − |
| 3 | 0.098 | − | − |
| 4 | 0.253 | − | − |
| 5 | 0.432 | ++ | ++ |
| 6 | 0.084 | + | + |
| 7 | 0.081 | + | + |
| 8 | 0.072 | + | + |
| 9 | 0.065 | − | − |
| 10 | 0.064 | − | − |

The presence of CMV proteins or beta$_2$m as detected by immunoblotting.

FIG. 13

Presence of CMV in the specific eluate after passage of urine containing the virus through a beta$_2$m affinity column as demonstrated by the characteristic viral protein profile on gel electrophoresis. Tracks 1 and 2 were loaded with high and low molecular weight markers (Sigma) respectively, of the molecular weights shown, and Track 3 with human beta$_2$m. Tracks 4–9 were loaded with fractions 5–10 from the affinity column (See Table 4), Tracks 10 and 11 with the infected urine before passage through the column and Track 12 with the flow through of the column.

EXAMPLE 4

Monoclonal antibodies directed against beta$_2$m, were capable of immunoprecipitating CMV as demonstrated by the presence of specific CMV DNA in the immunoprecipitates.

Tissue culture grown CMV was prepared as described in Experiment 6. The immunoprecipitation of the various virus preparations was carried out as described in Example 2 using the same monoclonal antibodies to beta$_2$m indicated in Table 5. The presence of specific CMV viral DNA was detected using cloned specific CMV DNA probes as follows:

The immunoprecipitates were boiled for 5 mins to separate the double stranded DNA 5 μl of this material was spotted onto nitrocellulose filters filters were soaked individually in the following solutions for the times indicated, air drying the filters between each step.

1×0.5M NaOH for 7 mins
2×0.6M NaCl/1.0M Tris pH 6.8 for 1 min
1×1.5M NaCl/0.5M Tris pH 7.4 for 5 mins
1×70% ethanol rinse only
2×chloroform rinse only
1×0.3M NaCl rinse only filters were allowed to air dry and then baked at 80° C. for 2 hours to fix the DNA to the filter.

$^{32}$P or Biotin labelled cloned CMV DNA probes (Oram et al 1982) obtained from P. Greenaway (Public Health Laboratory Service, Porton Down) were hybridized to the DNA on the filter by the following methods.

Hybridization filters were prehybridized for 3 hours at 37° C. in 45% formamide with 5×SCC[1] 5×Denhardts[2], 50mM sodium phosphate, 250 μg/ml sonicated salmon sperm DNA and 0.1% sodium dodecyl sulphate (SDS)

the biotin or $^{32}$P labelled Hind III O CMV probe was boiled for 5 mins to separate the double stranded DNA the above probe was hybridized to the nitrocellulose filters at 42° C. in a sealed bag overnight with shaking, in a solution as described above for the pre-hybridization but also containing 10% dextran sulphate and 100ng of the probe/ml.

[1]20×SCC consists of 3M NaCl, 0.3M Na Citrate at pH 7.4
[2]50×Denhardts consists of 1% Ficoll, 1% Polyvinyl pyrrolidine and 1% BSA detection using biotin labelled probes filters were then washed twice in 250ml of 2× SSC with 0.1% SDS for three mins at room temperature followed by two 30 min washes in 250ml of 0.4×SSC with 0.1% SDS at 50° C.

a blocking buffer of 0.25% BSA with 0.1M Tris Cl pH 7.5, 0.1m NaCl, 2mM MgCl$_2$ and 0.05% triton was added for 20 mins at 42° C.

filters were reacted with streptavidin (Bethesda Research Laboratories) at 2 μg/ml for b 10 mins with agitation filters were washed in the blocking buffer three times as above filters were incubated with poly (AP) (Bethesda Research Laboratories) at 1 μg/ml for 10 mins at room temperature with agitation filters were again washed three times with blocking buffer a dye solution consisting of nitro-blue tetrazolium plus S-bromo-4-chloro-3 indolyl phosphate (BRL biotin detection Kit) was added to the filters in a sealed bag, and left at room temperature for 4 hours with shaking to allow the colour reaction to develop.

filters were washed in 20mM Tris pH 7.5 with 5mM EDTA to terminate the colour reaction detection using $^{32}$P labelled "probes"

after the hybridization procedure filters were air dried and the presence of the $^{32}$P-probe detected by autoradiography using intensifying screens and pre-flashed film at −70° C. for at least 24 hours.

Results

Figures 14A, 14B:
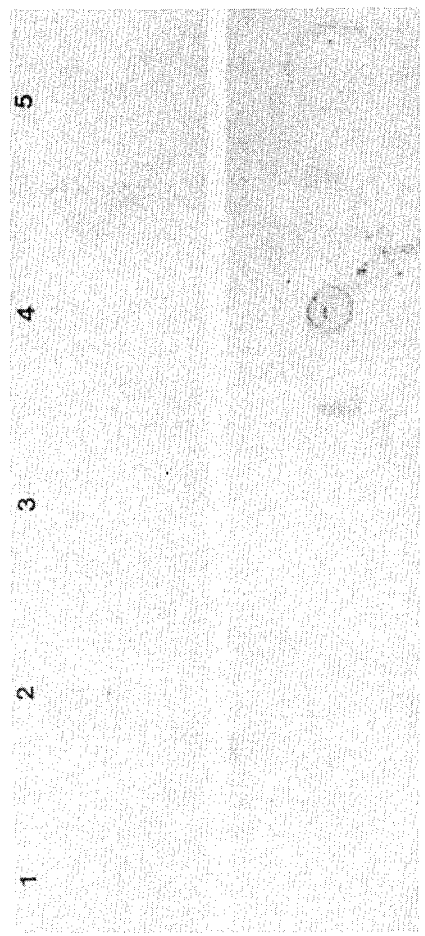
FIG. 14 is a hybridot showing the detection of CMV specific DNA using biotinylated cloned CMV probes after immunoprecipitation of tissue culture grown CMV with monoclonal antibodies to beta$_2$m.

Monoclonal antibodies against beta$_2$m were capable of immunoprecipitating CMV from tissue culture supernatants (either with or without added beta$_2$m) as shown by the ability to detect CMV specific DNA in the immunoprecipitates (FIG. 14, Table 5).

FIG. 14 is a hybridot showing the detection of CMV-specific DNA using biotinylated cloned CMV probes after immunoprecipitation of tissue culture grown CMV strain AD with monoclonal antibodies to beta$_2$m. The samples (virus with or without added beta$_2$m) and the monoclonal antibodies used for the immunoprecipitation are shown in Table 5, which summarizes the results of the DNA detection.

TABLE 5

Detection of CMV-specific DNA using biotinylated cloned CMV probes after immunoprecipitation of tissue culture grown CMV with monoclonal antibodies to beta$_2$m.

| Grid No[1] FIG. 12 | Sample[2] | Immunoprecipitated with monoclonal Ab | CMV DNA Detection |
|---|---|---|---|
| A1 | AD 169 + PBS | HLA-ABC-M2 | − |
| A2 |  | SRL-3 | + |
| A3 | AD 169 + 0.5 μl/ml beta$_2$m | HLA-ABC-M2 | − |
| A4 |  | SRL-3 | + |
| A5 | AD 169 + 0.25 μl/ml beta$_2$m | HLA-ABC-M2 | + |
| B1 |  | SRL-3 | +/− |
| B2 | AD 169 + 0.12 μg/ml beta$_2$m | HLA-ABC-M2 | + |
| B3 |  | SRL-3 | + |
| B4 | AD 169 | SLR-3 | + |
| B5 | λDNA | — | (+)[3] |

[1] The results are shown in FIG. 14 Virus was diluted 1 in 2 with PBS or PBS containing beta$_2$m at the concentration indicated with the exception of B3 which was a sample of undiluted virus.
[3] λDNA was labelled with biotin as a positive control for the DNA detection. (+) refers to detection of DNA.

The references in the text above are the following:
Davey P.G. et al, 1982 Clin. Chem. 28, 1330–1333.
Eurin, P.E., et al 1972 Scand. J. Clin. Lab. Invest. 29, 69–74.
Oram, J.D. et al 1982, J. Gen. Virol. 59, 111.
Pereira, L. et al, 1982, Infect. Immun. 36, 924–932.
Farrar, G et al, 1984, J. Gen. Virol. 65, 1991–2001.
Fraker, P.J. et al, 1978, Biochem & Biophys. Res. Comm. 80, (4), 849–857.
Laemmli, U. 1970, Nature 227, 680.
Talbot & Almeida, 1977, J. Gen. Virol. 36, 345–349.
Towbin et al, 1979, Proc. Nat. Acad. Sci. 76, 4352.

We claim:

1. A method of detecting a virus of the herpes group or an antibody to said virus in a clinical sample containing a beta$_2$m microglobulin (beta$_2$m), said method comprising:
    (1) removing beta$_2$m from the sample prior to the assay, or contacting the sample with a reagent reactive with beta$_2$m to form an anti-beta$_2$m-/beta$_2$m/virus conjugate, and
    (2) detecting the presence of said virus or antibody to said virus, wherein the reagent is a beta$_2$m-free reagent.

2. A method according to claim 1 wherein both the sample is freed from beta$_2$m and the reagent is free from beta$_2$m.

3. A method according to claim 2 wherein the clinical sample is a urine sample, and beta$_2$m is removed from said sample prior to the assay by maintaining a temperature of 35 to 40 C and a pH of 5.0 to 7.0 for at least 1 hour to permit endogenous enzymes to degrade the beta$_2$m.

4. A method according to claim 3 wherein the pH is approximately 5.5.

5. A method according to claim 3 wherein the presence of viral surface antigens is detected by enzyme-linked immunosorbent assay (ELISA).

6. A method according to claim 3 wherein the presence of viral surface antigens is detected by radioimmunoassay of an immunofluorescent technique.

7. A method according to claim 1 wherein the virus is Cytomegalovirus (CMV).

8. A method according to claim 1 wherein the reagent reactive with beta$_2$m an antibody, and said antibody binds to said beta$_2$m.

9. A method according to claim 8 wherein the antibody which binds to beta$_2$m is a monoclonal antibody reactive with beta$_2$m, said monoclonal antibody also being bound to a solid support.

10. A method according to claim 9 wherein said insoluble monoclonal antibody binds to a beta$_2$m-virus complex to form an antibody-viral conjugate, and the antibody-viral conjugate is separated from the sample.

11. A method according to claim 9 wherein the virus is disrupted by a cationic or nonionic detergent.

12. A method according to claim 11 wherein the presence of the virus is determined by detection of viral DNA.

13. A method according to claim 9 wherein after the beta$_2$m is bound to the monoclonal antibody, the presence of the virus is detected by identification of viral proteins.

14. A method according to claim 13 wherein the virus proteins are identified by immunoprecipitating the virus and detecting the virus proteins using antibodies to the virus antigens.

15. A method according to claim 14 wherein the virus is immunoprecipitated using staphyloccocal Protein A bound to sepharose or streptavidin bound to agarose.

16. A method according to claim 14 wherein the antibody is the antibody to CMV.

17. A method according to claim 15 wherein the beta$_2$m-free reagent which detects the presence of the antibody comprises an antigen bound to a solid support, said antigen prepared from a virus of the herpes group prepared in media free from beta$_2$m.

18. A method according to claim 17 wherein the presence of antibody is detected using an enzyme-linked immunoabsorbent assay (ELISA).

19. A method according to claim 1 wherein the beta$_2$m is removed from the clinical sample by filtering the sample through a membrane which allows passage of beta$_2$m but retains immunoglobulin molecules.

20. A method according to claim 1 wherein the beta$_2$m is removed from the clinical sample by using a polyclonal or monoclonal anti-beta$_2$m antibody to bind to the beta$_2$m in the sample and removing the beta$_2$m-antibody conjugate.

21. A method according to claim 1 in which the clinical sample is urine, blood, saliva or bronchoalveolar lavage fluid.

* * * * *